United States Patent [19]

Fienberg et al.

[11] Patent Number: 5,777,195
[45] Date of Patent: Jul. 7, 1998

[54] KNOCKOUT MUTANT MOUSE FOR DARPP-32 AND USE THEREOF

[75] Inventors: Allen A. Fienberg; Paul Greengard, both of New York, N.Y.

[73] Assignee: The Rockefeller University, New York, N.Y.

[21] Appl. No.: 649,103

[22] Filed: May 17, 1996

[51] Int. Cl.$^6$ .................... C12N 5/00; C12N 5/06; C12N 15/09; A61K 49/00

[52] U.S. Cl. .................... 800/2; 424/9.1; 424/9.2; 435/172.3; 435/325; 800/2; 800/DIG. 1; 800/DIG. 2; 800/DIG. 4; 800/DIG. 6; 935/34; 935/70

[58] Field of Search .................... 800/2; 424/9.1, 424/320.1, 9.2; 435/172.3, 325

[56] References Cited

U.S. PATENT DOCUMENTS 5,464,764  11/1995  Capecchi et al. .............. 435/172.3
5,470,560  11/1995  Martin, Jr. .................... 424/902

OTHER PUBLICATIONS

Nestler, E. (1994), Cell 79, 923–926.
Lemard, W. et al (1995). Immunological Reviews 148, 97–114.
Balk, J–H et al (1995). Nature 377, 424–428.
Drago, J. et al (1994). Proc. Natl. Acad. Sci. USA 91, 12564–68.
Girault, J–A et al (1989). Proc. Natl. Acad. Sci. USA 86, 2493–97.
Raisman–Votani, R. et al (1990). Brain Research 507, 45–50.
Seeman, P. et al (1994) Trends: Pharmacological Sciences 15, 264–70.
Capecchi, M. (1994). Scientific American, Mar. 1994, 34–41.
Brené, S. et al (1994). The Journal of Neuroscience 14, 985–998.

Westphal, H. (1989). FASEB J. 3, 117–120.
Accili et al. (1996) Proc. Natl. Acad. Sci. USA 93, 1945–49.
Aperia et al. (1992) Proc. Natl. Acad. Sci. USA 89, 7394–7397.
Balk et al. (1995) Nature 377:424–8.
Bertorello et al. (1990) Nature 347(6291), 386–8.
Caine et al. (1995) Behav. Pharm.6:333–347.
Caine et al. (1994) J. Experimental Analysis of Behavior 61(2), 213–21.
Calabresi et al. (1987) Neuroscience 20(3), 757–71.
Drago et al. (1994) Proc. Natl. Acad. Sci. USA 91, 12564–8.
Girault et al. (1986) Neuroscience 19(4), 1109–1117.
Giros et al. (1996) Nature 379:606–12.
Hanson et al. (1987) Eur. J. Pharm. 144, 245–246.
Hope et al. (1992) Proc. Natl. Acad. Sci.USA 89(13), 5764–8.
Joyner, A. L. (1993) Gene Targeting: A Practical Approach. The Practical Approach Series (Rickwood et al., Eds.), IRL Press, Oxford.
Korner et al. (1994) Diabetes 43, 629–633.
Kosten et al. (1994) J. Pharmacol. Exp. Ther. 269, 137–144.
Ridley, R. M. (1994) Prog. Neuro. 44, 221–231.
Surmeier et al. (1995) Neuron 14, 385–397.
te Riele et al. (1992) Proc. Natl. Acad. Sci. USA 89, 5128–5133.
Walaas, S. I., D. W., A., and P., G. (1983) Nature 301, 69–71.

(List continued on next page.)

*Primary Examiner*—Brian R. Stanton
*Attorney, Agent, or Firm*—Klauber & Jackson

[57] ABSTRACT

A knockout mouse containing a non-functional allele for the gene that naturally encodes and expresses functional DARPP-32 is disclosed. This mouse contains two non-functional alleles for the gene that naturally encodes and expresses functional DARPP-32, and therefore is unable to express functional DARPP-32. This mouse finds utility as a screening model for potential therapeutic agents useful in the treatment of schizophrenia, Parkinson's disease, and the treatment of addictions, especially those involving drugs of abuse.

15 Claims, 11 Drawing Sheets

OTHER PUBLICATIONS

Wan et al., *Psychopharmacology* 120:433–441 (1995).
Xu et al. (1994) Cell 79:729–42.
Xu et al. (1994) Cell 79:945–55.
Zhou et al. (1995) Cell 83:1197–209.
Birnstiel et al. (1985) Cell 41:349–59.
Daniel et al. (1991) J. Neurosci. 11:1907–17.
Dolan et al. (1995) Nature 378:180–2.
Elliot et al. (1995) Psychol. Med. 25:619–30.
Goetz et al. (1992) Neurol. Clin. 10:527–40.
Okubo et al. (1997) Nature 385:634–6.
Owen et al. (1993) Brain 116:1159–75.
Sedvall et al. (1995) Clin. Neurosci. 3:112–21 (Abst.).
Volkow et al. (1997) Nature 386:830–3.
Weinberger et al. (1986) Archs. Gen. Psychiat. 43:114–24.

KNOCKOUT MUTANT MOUSE FOR DARPP-32 AND USE THEREOF

GOVERNMENTAL SUPPORT

The research leading to the present invention was supported in part by the National Institute of Mental Health grant MH 40899. The government may have certain rights in the present invention.

TECHNICAL FIELD OF THE INVENTION

This invention relates generally to a mouse constructed to lack a functional copy of the gene coding for DARPP-32 and to methods of making and using the same including as an animal model for testing novel therapeutic strategies and therapeutic agents for treating diseases such as schizophrenia and Parkinson's Disease.

BACKGROUND OF THE INVENTION

Numerous physiological processes are regulated by the mechanism of protein phosphorylation. This basic enzymatic reaction refers to the transfer of a phosphate molecule from adenosine triphosphate to a target molecule by the action of an enzyme called a protein kinase. Addition of a phosphate molecule to a target protein can change the structure of that target protein and thus alter its activity. The opposite reaction involving the removal of a phosphate molecule is mediated by an enzyme called a phosphatase. The phosphorylation/dephosplhorylation of proteins is involved in diverse cellular processes and provides an exquisitely sensitive and reversible means of regulating cellular function.

One of the main tasks in attempting to understand brain function is to elucidate how neurotransmitters such as dopamine act to regulate neuronal cell function. Neurotransmitters act by binding to specific receptors on the outside of the cell and transmit signals to proteins on the inside of the cell in a process called signal transduction. Numerous studies have indicated that regulation of the activity of protein kinases and phosphatases is involved in signal transduction. The study of signal transduction mechanisms mediated by phosphorylation/dephosplhorylation includes determining how the various kinases and phosphatases are regulated by molecules outside the cell, and how the signal is transmitted from the protein kinase or phosphatase to various target protein substrates within the cell.

In a search for various protein kinase substrates that might be localized to specific neuronal subtypes, Greengard and colleagues (1) discovered a dopamine and cyclic AMP regulated phosphoprotein having a molecular weight of 32,000 Kd (DARPP-32). DARPP-32 is highly enriched in cell bodies of the neostriatum as well as in nerve terminals in the globus pallidus, and substantia nigra which are target regions for neurons of the neostriatum. Lower levels of DARPP-32 are found in the nucleus accumbens, cortex, olfactory tubercle, choroid plexus and kidney. Subsequent studies have shown that dopamine activates a series of intracellular reactions leading to the phosphorylation of DARPP-32 by binding to the D1 subclass of dopamine receptor. The phosphorylation of DARPP-32 alters its biological properties converting the protein into a highly potent inhibitor of protein phosphatase-1. Since protein phosphatase-1 is a major protein phosphatase in the brain, this inhibitory role of DARPP-32 has considerable physiological significance. In addition to its relation to dopamine, to date, over eleven different signal transduction pathways have been shown to affect the DARPP-32/protein phosphatase-1 cascade in the striatum.

Gene targeting in embryonic stem cells is a relatively new technique that allows the precise manipulation of genes in vivo. This technique allows the creation of mice with defined mutations in the structure of any given gene. This ability to generate predetermined mutations gives investigators the ability to apply the power of genetics to complex neuronial systems as it has successfully been applied in such organisms as Drosophila and C. elegans.

Despite the recent advances in our study of the regulation of neuronal processes in the brain, treatment of many related preconditions and/or diseases remain inadequate. These ailments include addictions to alcohol, drugs and/or nicotine, and schizophrenia and Parkinson's Disease. Parkinsonian patients, for example, suffer from the death of neurons which provide dopamine as a neurotransmitter. The elucidation of the signal transduction pathways would allow new approaches to the development of novel anti-Parkinson therapeutic agents. These therapeutic agents would have their use in the activation of downstream components of the dopamine signaling cascade.

A key to finding treatments for many disorders has been the development of appropriate animal models. Unfortunately, to date few if any animal models exist for screening potential therapeutic agents that could be used in the treatment of addictions to alcohol, drugs and/or nicotine, and schizophrenia and as eluded to above, Parkinson's Disease.

Definitions

"Gene targeting" is a type of homologous recombination that occurs when a fragment of genomic DNA is introduced into a mammalian cell and that fragment locates and recombines with endogenous homologous sequences.

A "knockout mouse" is a mouse that contains within its genome a specific gene that has been inactivated by the method of gene targeting. A knockout mouse includes both the heterozygote mouse (i.e., one defective allele and one wild-type allele) and the homozygous mutant (i.e., two defective alleles).

The term "addictive drug" encompasses substances known to be addictive in humans including but not limited to amphetamines, morphines, cocaine and its related derivatives, alcohol and nicotine.

A "marker gene" is a selection marker that facilitates the isolation of rare transfected cells from the majority of treated cells in the population. A non-comprehensive list of such markers includes neomycin phophotransferase, hygromycin B phophotransferase, Xanthiline/guanine phosphoribosyl transferase, herpes simplex thymidine kinase, and diphtheria toxin.

SUMMARY OF THE INVENTION

The present invention includes a knockout mouse containing a non-functional allele for the gene that naturally encodes and expresses functional DARPP-32. Included within this aspect of the invention is a knockout mouse containing two non-functional alleles for the gene that naturally encodes and expresses functional DARPP-32, and therefore is unable to express functional DARPP-32.

Non-functional alleles can be generated in any number of ways that are well known in the art, all of which may be used in the present invention. In some embodiments, a non-functional allele is made defective by an insertion of extraneous DNA into the coding region DARPP-32 allele. In a preferred embodiment, the insertion is placed in the first exon of the coding region of the DARPP-32 gene. In more preferred embodiments, the insertion contains a signal to terminate transcription prior to the transcription of a region of the allele that encodes DARPP-32. In these preferred embodiments it is still more preferred to remove a section of DNA at the beginning of the coding region for DARPP-32 and replacing it with the above insertion.

The present invention includes a knockout mouse with a phenotype that comprises a diminished response to dopamine. In some embodiments this diminished response can be measured by an altered modulation of calcium channel function by dopamine, in situ. In other embodiments this diminished response to dopamine can be measured as a loss of dopamine inhibition of the sodium-potassium ATPase (Na,K ATPase) in situ. In still other embodiments the diminished response to dopamine is evidenced by an increased excitability of striatal and cortical neurons. Preferred embodiments show two of these three characteristics and in more preferred embodiments all three characteristics are evident.

In certain embodiments of the present invention one or more additional characteristics are also found. They include (a) a diminished release of dopamine in response to amphetamines as determined in situ; (b) a diminished release of GABA (4-Aminobutyric acid) in response to amphetamines as determined in situ; (c) an increased level of substance P in the striatum and cortex as determined in situ; (d) an increased level of neurotensin in the striatum and cortex as determined in situ; (e) an attenuated increase in locomotor activity in response to cocaine in vivo; (f) an attenuated increase in the protein Fos in response to an amphetamine as determined in situ; (g) an attenuated increase in the protein Chronic Fos Related Antigen (FRA) in response to cocaine as determined in situ; (h) a loss of inhibition of the activity of the brain sodium-potassium-ATPase in response to dopamine as determined in situ; (i) a loss of inhibition of the activity of the renal sodium-potassium-ATPase in response to Atrial Natriuretic Factor as determined in situ; and (j) a loss of Atrial Natriuretic Factor (ANF) mediated increases in sodium excretion in vivo. The present invention envisions and includes embodiments that have all possible combinations of these additional characteristics including a preferred embodiment having them all.

The present invention also includes a method for producing the knockout mouse of the instant invention that includes: obtaining genomic DNA encoding DARPP-32 constructing a vector containing said genomic DNA and a marker gene wherein said marker gene is placed within the exon of said genomic DNA. The vector is then electroporated into an embryonic stem cell and an embryonic stem cell is selected that has integrated the vector into the genome, wherein the selected cell has integrated the marker gene into the endogenous site of the gene for DARPP-32 in the mouse genome. The cell is then injected into a mouse blastocyst which is then re-implanted into a pseudopregnant female mouse, which gives birth to a chimeric mouse containing a defective allele for DARPP-32 in its germ line. The chimeric mouse is then mated to a mouse of a standard in-bred line to generate a heterozygous knockout mouse. Two heterozygous mice are then bred generating a homozygous knockout mouse offspring.

Another aspect of the invention is a method for selecting a therapeutic agent for possible use in the treatment of schizophrenia which comprises administering a suspected therapeutic agent to the knockout mouse of the present invention and measuring and/or determining the putative therapeutic agent's effect on any of the phenotypic characteristics outlined above which may be believed to be related to schizophrenia.

A preferred embodiment of this aspect of the invention includes administering a suspected therapeutic agent to the knockout mouse of the present invention and measuring a test response to dopamine for the knockout mouse, wherein the normal response of the knockout mice in the absence of a therapeutic agent is characteristically different than that of wild-type mice. The potential therapeutic agents are selected on the basis of whether there is a statistical significance between test response and the normal response. Potential therapeutic agents are selected that show a statistically significant change in the characteristic measured/ determined. In a preferred embodiment, the normal response of the knockout mice in the absence of a therapeutic agent is characteristically different by being characteristically lower than that of wild-type mice and the selected therapeutic agents act to raise the sensitivity of that characteristic.

A still further aspect of the invention is a method for selecting a therapeutic agent for possible use in the treatment of Parkinson's disease which comprises administering a suspected therapeutic agent to the knockout mouse of the present invention and measuring and/or determining the putative therapeutic agent's effect on any of the phenotypic characteristics outlined above which may be believed to be related to Parkinson's disease.

The potential therapeutic agents are selected on the basis of whether there is a statistical significance between test response and the normal response. Potential therapeutic agents are selected that show a statistically significant change in the characteristic measured/determined. In a preferred embodiment, the normal response of the knockout mice in the absence of a therapeutic agent is characteristically different by being characteristically lower than that of wild-type mice and the selected therapeutic agents act to raise the sensitivity of that characteristic.

Yet another aspect of the present invention is a method for selecting a therapeutic agent for possible use in the treatment of addictive behaviors which comprises administering a suspected therapeutic agent to the knockout mouse of the present invention and measuring and/or determining the putative therapeutic agent's effect on any of the phenotypic characteristics outlined above which may be believed to be related to Parkinson's disease.

In this method, the potential therapeutic agents are selected on the basis of whether there is a statistical significance between test response and the normal response. Potential therapeutic agents are selected that show a statistically significant change in the characteristic measured/determined are selected. In a preferred embodiment, the normal response of the knockout mice in the absence of a therapeutic agent is characteristically different by being characteristically lower than that of wild-type mice and the selected therapeutic agents act to raise the sensitivity of that characteristic.

Still another aspect of the instant invention involves a method for selecting a therapeutic agent for possible use in the treatment of hypertension by administering a suspected therapeutic agent to a knockout mouse of the invention, measuring a test response to Atrial Natriuretic Factor for said knockout mouse; wherein the normal response of knockout mice in the absence of a therapeutic agent is characteristically different than that of wild-type mice. The therapeutic agent can then be selected by comparing the test response to the normal response, wherein a therapeutic agent is chosen when the test response is statistically significantly different than the normal response. In a preferred embodiment, the normal response of knockout mice in the absence of a therapeutic agent is characteristically different by being characteristically lower than that of wild-type mice.

The suspected therapeutical agents may be obtained from any of several commercial drug libraries currently being licensed by Chemical companies. Preferred suspected therapeutical agents include agonists and antagonists to dopamine receptor subtypes (D1–D5) or to known glutamate receptor subtypes.

BRIEF DESCRIPTION OF THE DRAWINGS

FIGS. 1A–C are illustrations wherein FIG. 1A shows the intron-exon structure of the wildtype DARPP-32 gene. FIG. 1B illustrates the targeting vector constructed to inactivate the DARPP-gene. FIG. 1C illustrates the structure of the DARPP-32 gene after homologous recombination with the targeting vector.

In FIG. 1D, the bottom and middle panel illustrate immunoblots comprising protein prepared from the striatum and cortex of mice and probed with a DARPP-32 specific antibody. Note the absence of a band from mice that have the mutant genotype.

FIG. 2E shows that there was no difference in the response to the initial application of the D1 agonist between wildtype, heterozygote and mutant mice. However, mutants (FIG. 2F) displayed significantly less reversal of the modulation ($p<0.05$, Kruskal-Wallis ANOVA) than either wildtype or heterozygotes.

FIGS. 4A and 4B are graphs wherein FIG. 4A shows the effect of amphetamine on GABA release showing that mutant (GABA-M) mice release less GABA than wildtype mice (GABA-W). DARPP-32 mutants (DA-M) display lower levels of dopamine release as compared to wildtype mice (DA-W), and FIG. 4B illustrates lower levels of GABA release in response to dopimine seen in mutant (GABA-M) mice vs. wildtype mice (GABA-W).

DESCRIPTION OF THE INVENTION

Figures 1A, 1B, 1C:
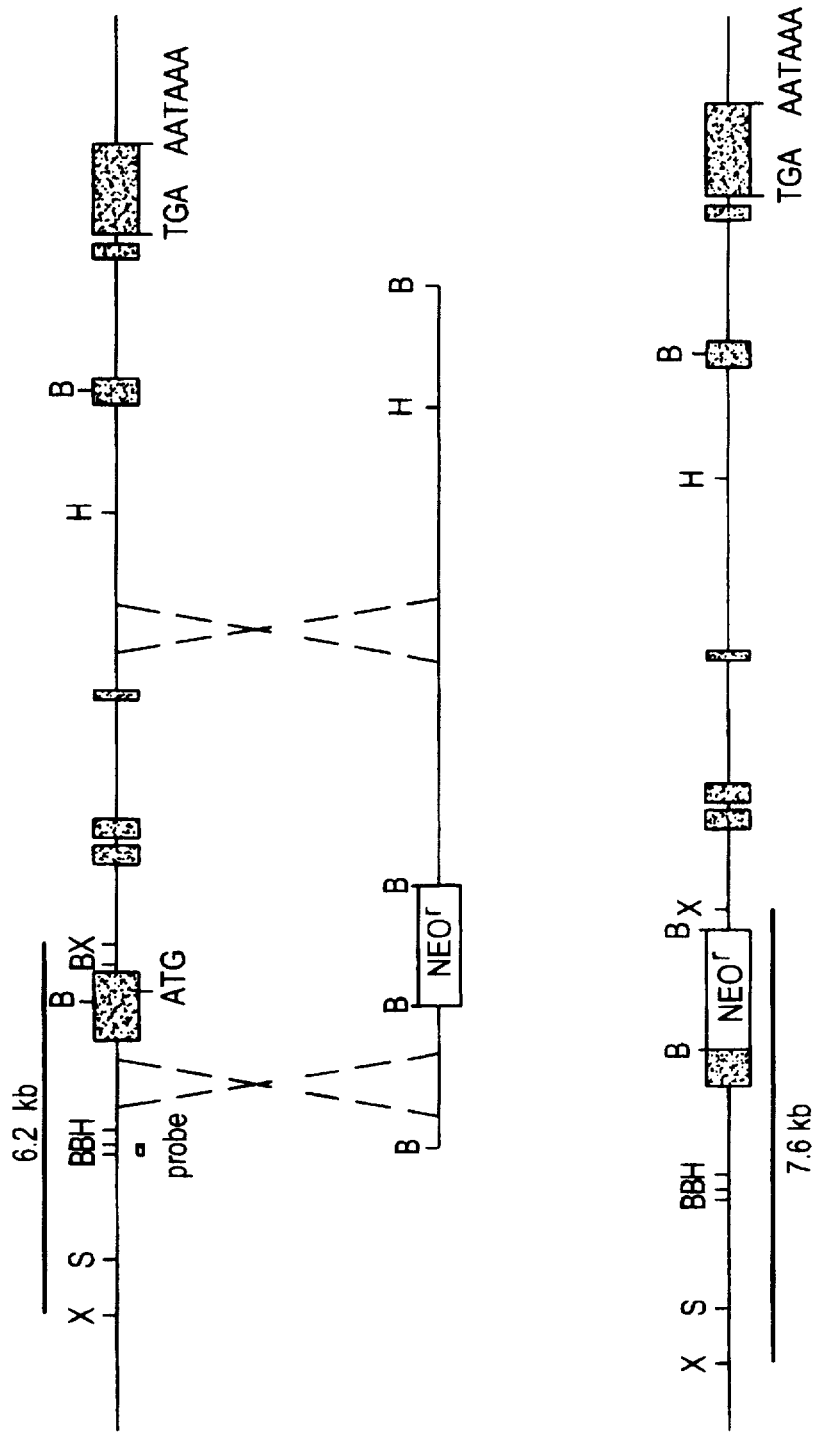

The present invention concerns a knockout mouse lacking a functional copy of the gene coding for the protein called DARPP-32 (for dopamine and cyclic AMP regulated phosphoprotein of molecular weight 32 kilodaltons). More particularly, this invention concerns a knockout mouse which allows the elucidation of the function of DARPP-32 in intact animals. Animals lacking DARPP-32 display several defects in several neuronal processes.

Diseases such as schizophrenia and Parkinson's disease involve alterations in dopamine signal transduction mechanisms, so that mice lacking DARPP-32 provide a convenient and facile animal model for the study and testing of novel therapeutic strategies and therapeutic agents. Additionally, since addictive drugs, especially the drugs of abuse such as cocaine and heroin, act to alter normal dopamine signaling pathways such that the normal physiological process of reward is redirected towards drug-taking behavior. The knockout mouse of the instant invention lacking functional DARPP-32 thus shows an altered response to addictive drugs and therefore a useful tool in the development of therapeutic agents aimed at controlling addiction.

Present therapeutic strategies aimed at alleviating the symptoms of neurological and psychiatric diseases such as schizophrenia involve the development of agonists or antagonists of the known dopamine receptors. The development of more efficacious drugs has been hampered by the known side effects of drugs that act at this membrane receptor level. The normal regulatory processes occurring in neurons are altered in mice lacking DARPP-32. In the mouse of the instant invention, the levels of dopamine and GABA release are lower than seen in wild type, normal animals. Also advantageously, the mutant mice of the instant invention exhibit increases in two key neurotransmitters, substance P and neurotensin. Thus, the model mouse has an altered normal physiological regulation of the neuronal system in a novel way such that the animal or tissues derived from it can be utilized for screening of potential therapeutic agents and/or therapeutic regimens that act at the intracellular level, especially neurotransmitters that interact with a dopamine signalling pathway. Neurotransmitters of this type are those such as glutamate, GABA, and nitric oxide. Drugs that can reverse any of the defects exhibited by the knockout mouse act at some point in the intracellular signaling cascade and are thus of potential use therapeutically. Additionally, since some defects occur at the behavioral level, the affectation or alteration of these can have a high predictive value for therapeutic use in modification of such behaviors.

The animal model of the instant invention thus finds particular utility as a screening tool to elucidate the mechanisms of the various protein phosphorylation steps involved in both normal and diseased patient populations. This model can thus be utilized to assess the response to a variety of potential therapeutic strategies and therapeutic agents which can thus be used in the treatment of patients suffering from a variety of neurological diseases and disturbances.

Using mice of the present invention, various small molecule drugs can be screened for potentially advantageous effects, including enhanced potency as well as minimization of side effects. Typical candidates for such screening may be obtained from any of several commercial drug libraries currently being licensed by Chemical companies. Especially preferred suspected therapeutic agents include compounds which also exhibit agonist or antagonistic activity to dopamine receptor subtypes (D1-D5) or to known glutamate receptor subtypes.

Specific neurological and behavioral diseases for which this animal model can be utilized are addictions to alcohol, drugs and/or nicotine, and schizophrenia and Parkinson's Disease. By utilizing the various characteristic responses of the mouse to endogenous and exogenous agents, and comparing these responses to a mouse treated with a potential therapeutic agent, an assessment of the utility of the potential therapeutic agent in a particular disease state can be made. For instance, the potential therapeutic agent can be administered to the mouse model of the instant invention, and its response to dopamine can be monitored. Comparison with the response to dopamine in a normal, wild-type mouse can then provide an indication of the value of the potential therapeutic agent.

The mouse of the instant invention lacking DARPP-32 exhibits a number of differences in the basic processes in the neurons. Additionally, a number of behaviors displayed in the mouse in response to drugs of abuse demonstrate the utility of this animal in examining the possible mechanisms and role for DARPP-32 as a biological target for the mechanism of drugs of abuse. Finally, since DARPP-32 is also expressed in the kidney, mice lacking DARPP-32 display several alterations in renal function.

The animal of the instant invention is preferably a mouse, since mice offer distinct advantages as laboratory research animals. However, it will be recognized that any other animal having the DARPP-32 protein will be amenable to the methods of the instant invention.

The following examples are presented in order to more fully illustrate the referred embodiments of the invention. They should in no way be construed, however, as limiting the broad scope of the invention.

EXAMPLES

Example 1

The Method for Constructing DARPP-32 Mouse

A. Cloning of the DARPP-32 Gene and Construction of the Targeting Vector

Bacteriophage clones with genomic DNA containing the exons encoding the DARPP-32 gene are first obtained by standard library screening methods (2). Once purified the genomic DNA is then cut with restriction enzymes and the locations of exons are determined by hybridization to the cDNA. The region of the gene containing the first exon is sequenced in order to verify its identity unambiguously. A restriction map of the complete DARPP-32 gene is shown in FIG. 1A.

B. Design and Construction of the Targeting Vector

The targeting vector is a plasmid molecule constructed so as to contain large fragments of genomic DNA flanking a selectable marker gene, typically the gene encoding neomycin resistance. In addition, this plasmid is also constructed so as to delete some specific part of the gene required for function. When transferred into cells this plasmid recombines with chromosomal DNA at the endogenous location of the gene in a process termed homologous recombination. The plasmid also recombines with the chromosomal DNA at other sites in the genome. Therefore one must be able to distinguish homologous recombination events which are rare from non-homologous recombination events which occur much more frequently. The ratio of homologous to nonhomologous events varies with each gene from 1:20 to 1:6000. Factors that influence this ratio are the amount of DNA in the targeting vector and the strain of mouse that is used as the source of DNA for the targeting vector (3). To mutate the DARPP-32 gene a plasmid vector is constructed which contains a neomycin resistance gene flanked by a 2.2 kilobase genomic DNA fragment of the DARPP-32 gene on one side and a 6.0 kilobase fragment of the DARPP-32 gene on the other side (see FIG. 1B). In addition, a 400 base pair fragment of DNA containing part of the first exon is not included in the construct.

C. Design of the Gene-Targeting Strategy

As described above one must be able to distinguish homologous from non-homologous integration events. To do this a fragment of DNA is characterized that must have the following characteristics: (a) the fragment of DNA must be located outside of the region of the DNA used to construct the targeting vector. This ensures that only the endogenous gene is followed in this screening procedure (b) this fragment of DNA must be free of repetitive sequences that would otherwise obscure its ability to hybridize to a single fragment of DNA in a genomic southern blot. With a knowledge of the restriction fragment pattern one uses this fragment of DNA in southern blot analysis in order to follow the size of a given fragment of DNA that should change in size when a homologous recombination event occurs at the endogenous site of the gene. In the DARPP-32 gene, a 300 base pair fragment located in a HindIII/Sal fragment just 5' to DNA in the targeting plasmid was chosen (see FIG. 1A "probe"). In wild type DNA this 300 base pair probe hybridizes to a 6.2 kilobase fragment of genomic DNA when this DNA is cut with the restriction enzyme Xba. When the above described targeting vector recombines with DNA at the DARPP-32 locus then the 6.2 kilobase fragment of DNA is enlarged to 7.6 kilobases. This shift in size is easily discernible by Southern blot analysis (see FIG. 1D—southern blot).

D. Isolation and Growth of Cells Comprising the Embryonic Feeder Layer

Mutation of a gene by homologous recombination is first accomplished in embryonic stem (ES) cells. These cells have the ability to become a part of the germline of an embryo if injected at an early stage. ES cells are grown on a feeder layer of embryonic fibroblasts (EF) which secrete unknown factors which keep the stem cells in an undifferentiated state. These fibroblasts are isolated and grown using the following protocol:

1. Set up timed matings between a neomycin resistant male mouse (typically a mouse with another knockout, if available) and several females.

2. Isolate about 5-10, 13-16 day old fetuses and wash with 50 ml of phosphate buffered saline (hereafter called "PBS").

3. Cut off the heads and remove the organs from the thorax and discard.

4. Wash the remaining tissue five times with PBS.

5. Mince finely with sharp scissors.

6. Add 5 ml of trypsin (0.25%) and incubate at 10 minutes at 37° C., shaking every two minutes. Pipette up and down vigorously.

7. Add 30 ml of EF medium, let the debris settle out and transfer the supernatant to a fresh tube.

8. Retrypsinize the debris and combine the supernatants.

9. Centrifuge for 5 minutes at 1500 rpm.

10. Resuspend the pellet in 100 ml of EF medium.

11. Plate out the supernatant in three T175 flasks (Corning).

12. Grow cells to confluency (1–4 days) and split into 10 T175 flasks, add G418 to 150 mg/ml and grow to confluency for 2–3 days.

13. Split cells into 30 T175 flasks still under G418 selection and grow to confluency.

14. Trypsinize cells and freeze the cells from one T175 flask/tube (about 30×106 cells).

Recipe for ES Medium: (for 500 ml)

75 ml fetal calf serum 2.5 ml 100×Gentamycin (Gibco)

5 ml 100×glutamine 5 ml 100 × non-essential amino acids (Gibco)

5 ml 100 × nucleosides 5 ml 100×2-mercaptoethanol (70 ml 2-mercaptoethanol in 100 ml PBS, filter: make new every two weeks)

400 ml DMEM (Gibco)

filter through an 0.2 m filter and store at 4° C.

Recipe for EF Medium (for 500 ml)

50 ml fetal calf serum 5 ml 100× pen-strep (Gibco)

5 ml 100× glutamine (Gibco)

450 ml DME with HEPES (Gibco)

filter through an 0.2 m filter and store at 4° C.

Recipe for 100× Nucleosides: (all components from Sigma)

80 mg adenosine 85 mg guanosine 73 mg cytidine 73 mg uridine 24 mg thymidine 100 ml water dissolve for 15 min at 65° C., filter, aliquot and store at −20° C.

E. To expand embryonic fibroblasts in preparation for the growth of embryonic stem cells 1. Day 0: Thaw 1 tube of 30×106 frozen embryonic fibroblasts and aliquot into three T175 flasks.

2. Day 4: split the cells into 10 T175 flasks

3. Day 7: inactivate the cells by mitomycin C treatment (1) Mitomycin treatment (a) dissolve I vial of mitomycin C (2 mg/vial, Sigma) in 10 ml of PBS (20× solution)

(b) feed EF cells with 1X mitomycin C in EF medium for 2 hrs (c) take off medium, wash three times in PBS (d) trypsinize the cells and freeze at 30×106 cells/ml (10 tubes of 1 ml)

F. Plating of Embryonic Fibroblasts

1. Treat tissue culture plates with 0.1% gelatin for at least 20 minutes at room temperature.

2. Remove gelatin.

3. Thaw EF cells at 37° C. add 10 ml of EF medium, spin and resuspend. One vial of mitomycin treated EF cells(30 ×106 cells) should be resuspended in 30 ml of EF medium.

4. Plate 500 ml per 24-well or 200 ml per 96-well, 5 ml for a T25 and 30 ml for a T175, 9m for a 10 cm dish.

5. Wait at least 4 hrs before plating ES cells.

G. Plating of embryonic stem cells

1. Obtain a vial of embryonic stem cells from an individual skilled in the art of their isolation and growth from 3.5 day old mouse blastocyst embryos (4).

2. Prepare a flask with mitomycin treated feeders the day before plating the ES cells. Feed the ES cells with ES medium and LIF (Leukemia Inhibitory Factor, BRL, 1000 U/ml) just before plating.

3. Thaw ES cells at 37° C., add 10 ml of ES medium, spin, resuspend in ES medium. About 3 ×106 cells should be plated in a T25 flask. The cells should reach confluency after 2–3 days.

4. ES cells are then split 1:7 in preparation for electroporation of the targeting vector.

Cells should be maintained in an undifferentiated state. Colonies should be relatively round and grow in three dimensions. Differentiated colonies can be detected by an irregular shape with flattened cells at the edge of the colonies.

H. Electroporation of embryonic stem cells with the targeting vector and growth of electroporated cells 1. The day before the electroporation 10×10 cm tissue culture dishes with EF should be prepared.

2. Linearize the targeting vector with a restriction enzyme that cuts the plasmid at only one site, (in the case of DARPP-32 use Not 1) ethanol precipitate the DNA, dry and then resuspend in 600 ml of PBS.

3. Trypsinize about 5×107 ES cells, resuspend in PBS containing the DNA and bring to 800 ml.

4. Add to cuvette (0.4 cm, # 165-2088, Biorad) and electroporate (Biorad Gene Pulser) using the following conditions (3.0 mF, 800 V).

5. Resuspend in 100 ml of ES medium containing LIF and plate in 10×10 cm plates with each plate containing 5 ×106 EF (no G418).

6. On Day 1 after plating, the media is changed to contain G418. Typically about 100–150 mg/ml is used.

7. Change the medium every day (with G418). Over the next few days most of the colonies will die leaving those that are resistant to G418. Pick colonies around day 6–8. After day 8 the colonies are usually too large and will start to differentiate.

I. Picking Colonies

1. The day before picking, 96 well plates with EF should be prepared. Change the medium with ES medium with LIF before picking.

2. Pick colonies under a microscope with a pipetman (P20). Pick only well-shaped and undifferentiated colonies.

3. Bring clones in 96-well U-bottom plates.

4. Add 15 ml trypsin, 5 minutes 37° C.

5. Add 35 ml medium (take medium from the 96-well plate with EF), pipette 10 times up and down and bring in 96 well plate (flat bottom) with EF.

6. Change the medium every day.

J. Passage of ES cells from 96- to 24 well plates

2–3 days after picking, the cells should be ready to split into two series of 24 well plates. One plate is used for freezing, the other plate is used for DNA analysis. The freezing plate should contain feeders, the plate for DNA preparation does not need feeders.

1. Aspirate the medium.
2. Add 50 ml trypsin. 5 min 37° C.
3. Add 150 ml of ES medium, pipette 10 times up and down.
4. Bring 100 ml in 24-well plate without feeders and 100 ml in 24-well plate with feeders.
5. Change the medium every day (the cells for DNA preparation can be changed with ES medium without LIF).

K. Freezing of the Clones

After two days the cells should be ready to freeze.

1. Aspirate the medium from the 24-well plates.
2. Add 1 ml of ice-cold freezing medium (90% fetal calf serum and 10% DMSO).
3. Seal the plate with parafilm and freeze at –70° C. The plates can be kept at this temperature for several months.

L. Preparation of Genomic DNA and Southern blot analysis

After five days the cells should be ready for preparation of genomic DNA.

1. Aspirate the tissue culture medium and add 500 ml of lysis buffer (100 mM Tris pH 8.5, 5 mM EDTA, 0.2% SDS, 200 mM NaCl, 100 mg proteinase K/ml) is added to each well of the plate.
2. The plate is then shaken overnight at 56° C. One volume of isopropanol is then added and the plate is swirled for 15 minutes at room temperature.
3. The DNA is then recovered by lifting the aggregated DNA precipitate from the solution using an eppendorf tip and placing the DNA in an eppendorf tube. Tubes are then spun briefly to pellet the DNA at the bottom of the tube.
4. The DNA is then dried and resuspended in 50 ml of TE buffer. The DNA is then dissolved overnight at 56° C.
5. The following day NaCl is added to a concentration of 0.2M and the DNA is precipitated with 100% ethanol. After drying the DNA is resuspended in 150 ml of TE.
6. 30 ml are then removed and digested with the restriction enzyme Xba. The restricted genomic DNA is then electrophoresed in a 0.8% agarose gel and southern blotted by standard procedures using flybond-N nylon blotting paper or any other suitable blotting paper (2).
7. Blots are hybridized in buffer containing 10% polyethylene glycol, 7% SDS, 1.5× SSPE (Maniatis et al.) and 0.1 mg/ml sonicated salmon sperm DNA at 65° C. for 12–16 hours. Blots are then washed in 2× SSC, 0.2% SDS for 15 minutes at room temperature, 1 X SSC 0.2% for 15 at room temperature, 0.5X SSC 0.2% SDS at 65° C. for 15 minutes and 0.2× SSC 0.2% SDS at 65° C. for 15 minutes. Blots are then exposed to X-ray film overnight.

M. Thawing and expansion of positive clones

1. Analysis of the southern blots will reveal which clones contain a mutated allele based on the predicted change as determined above under Section C. The wild type and mutated alleles should have equal intensities on the autoradiographic film since each is present in one copy. In addition the intensity of each allele should be approximately one half that of the wild type allele since in wild type DNA there are two copies of the allele. Clones that may have the mutated allele but in a reduced intensity should not picked to inject into embryos. These clones are likely to be contaminated with another wild type clone.

2. To thaw out any given clone, bring the tissue culture dish out on dry ice.
3. Using warmed ES media add 1 ml of media and pipette up and down. Suck off 1 ml and place it in a 15 ml sterile plastic tube. Add another ml of warmed media and suck up and down. Add one last ml to thaw the rest of the cells in the well. Plate this three ml into 2 wells of a 24 well dish.
4. Change the medium on days 2 and 3.
5. When 50% confluent, trypsinize the cells in I well and split into two wells of a 12 well plate. Freeze away the cells in the other well.
6. When cells in the 12 well dish are confluent, cells in one of the wells are frozen while cells in the other well are split into two wells of a 6-well plate.
7. When confluent, 1–1.5 of the cells in the 6-wells are split into 2 T25. The rest of the cells from the 6-well are frozen. When confluent, cells in the two T25s are frozen back into 10 cryovials.

N. To prepare cells for injection 1. 48 hrs before injection gelatinize the wells in a 24 well dish
2. Thaw one vial and plate into one well of a 24 well dish. Refeed each day.
3. On the day of injection, refeed 2 hrs before injection
4. Trypsinize cells, replate on a gelatinized plate in order to remove feeder cells. Wait 30–60 minutes. Suck up cells and transfer tan eppendorf tube. Cells are now ready for injection.
5. Cells are injected into early mouse embryos by an individual skilled in the art. References for these procedures are given in (4)

O. Scoring for Germline Transmission

Figure 1D:
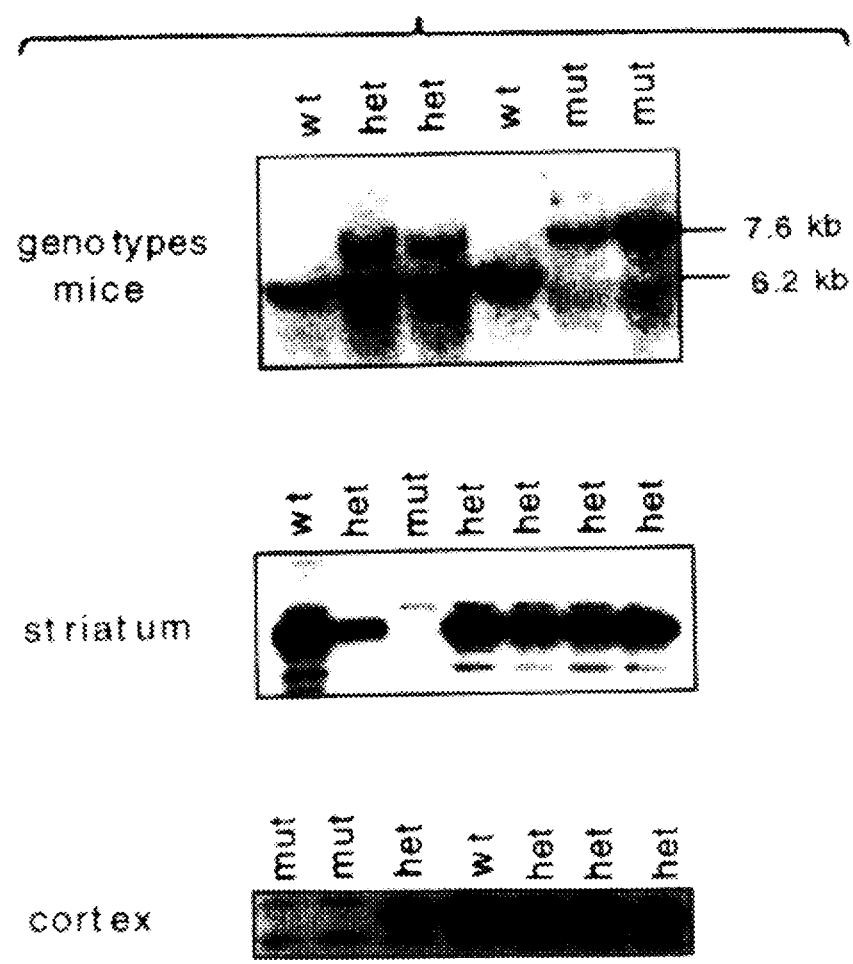
FIG. 1D is a southern blot wherein the top panel illustrates a southern blot of a litter of mice born from a mating of heterozygotes. Note the three genotypes and the disappearance of the wildtype band in the mutants.
Figure 2A:
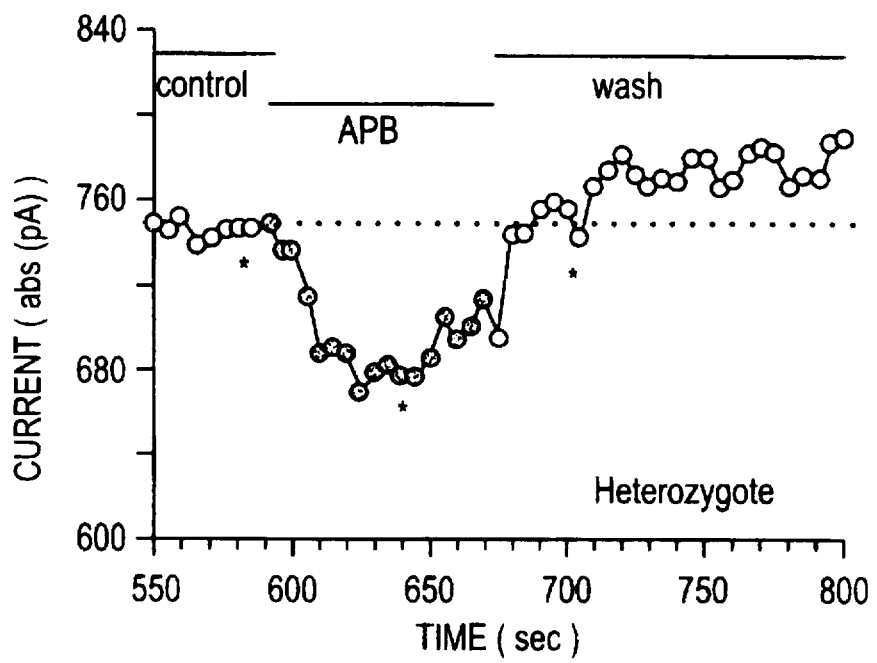
FIGS. 2A–F show the effect of 6-chloro-APB (APB) a D1 agonist on the activity of voltage dependent calcium channels measured in wild-type mice (FIGS. 2A and 2B) or in DARPP-32 knockout mice (FIGS. 2C and 2D).
Figure 2B:
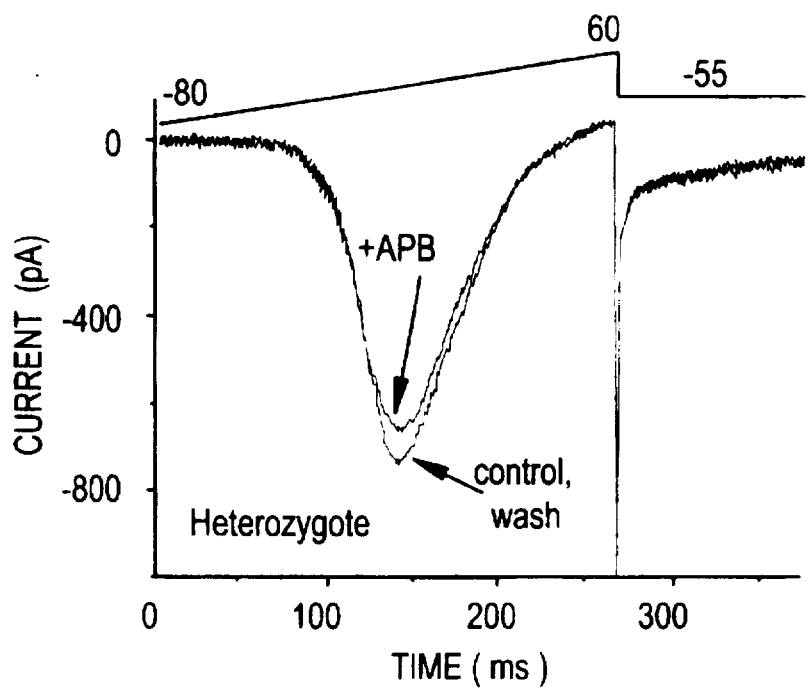
Figure 2C:
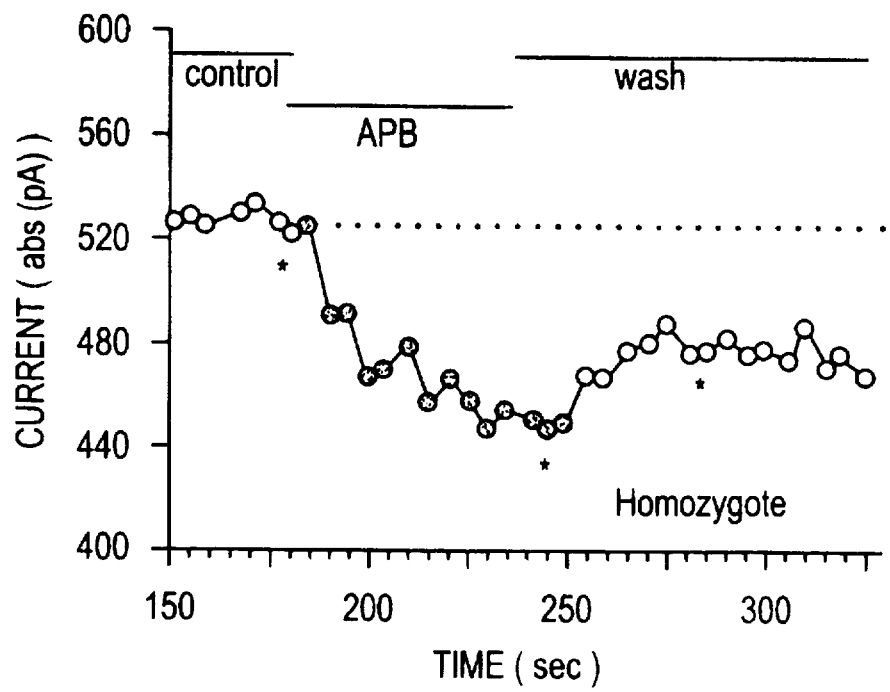
Figure 2D:
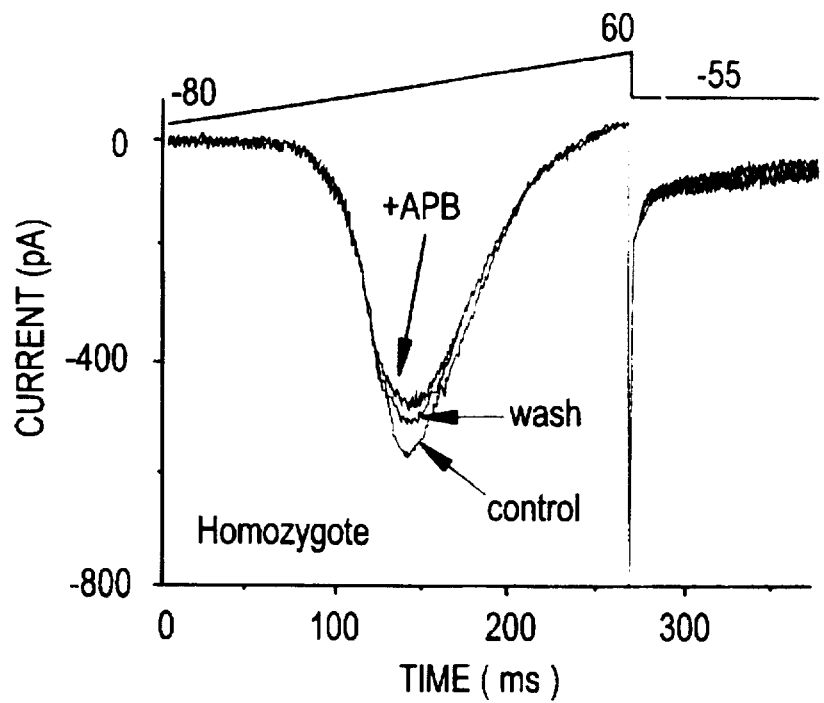
Figure 2E:
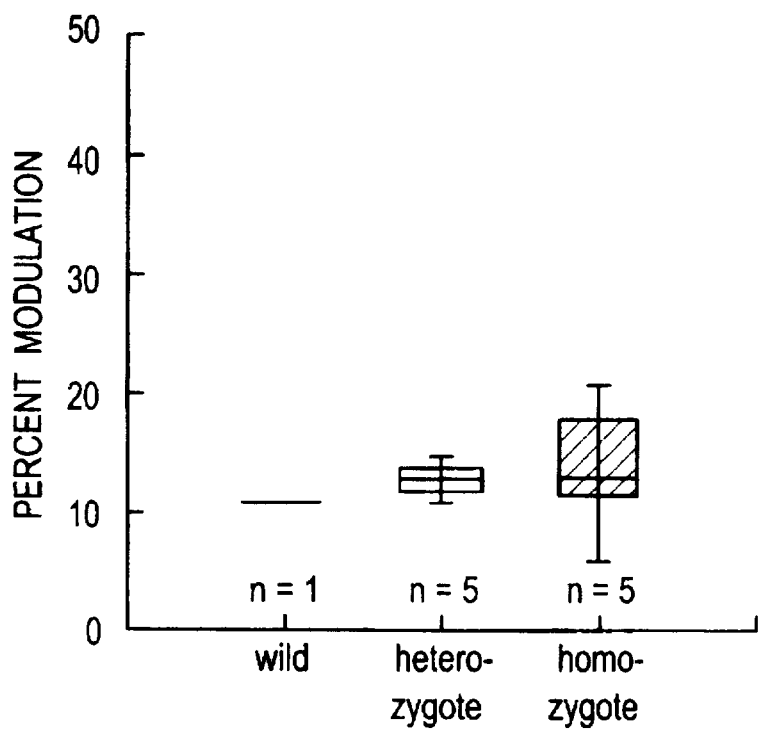
Figure 2F:
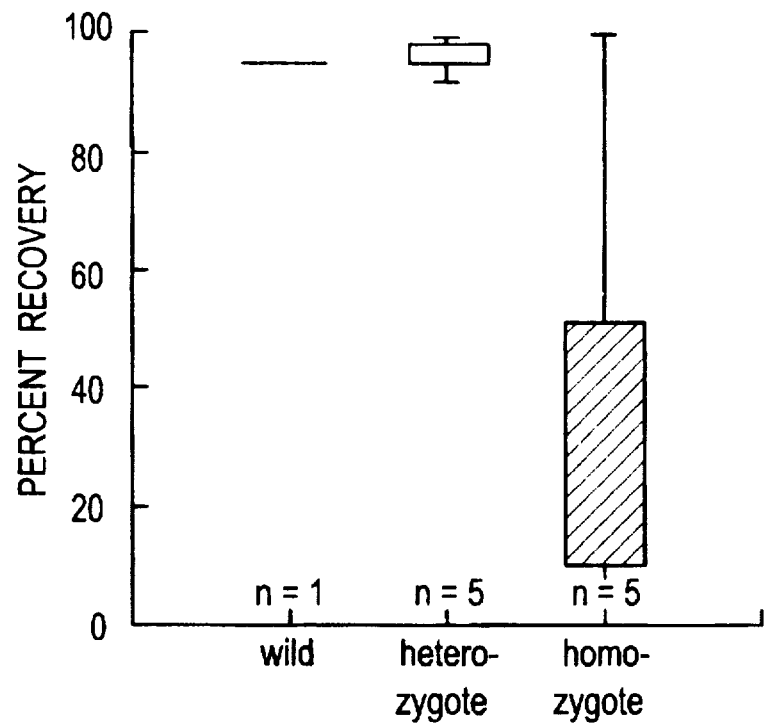
Figure 3:
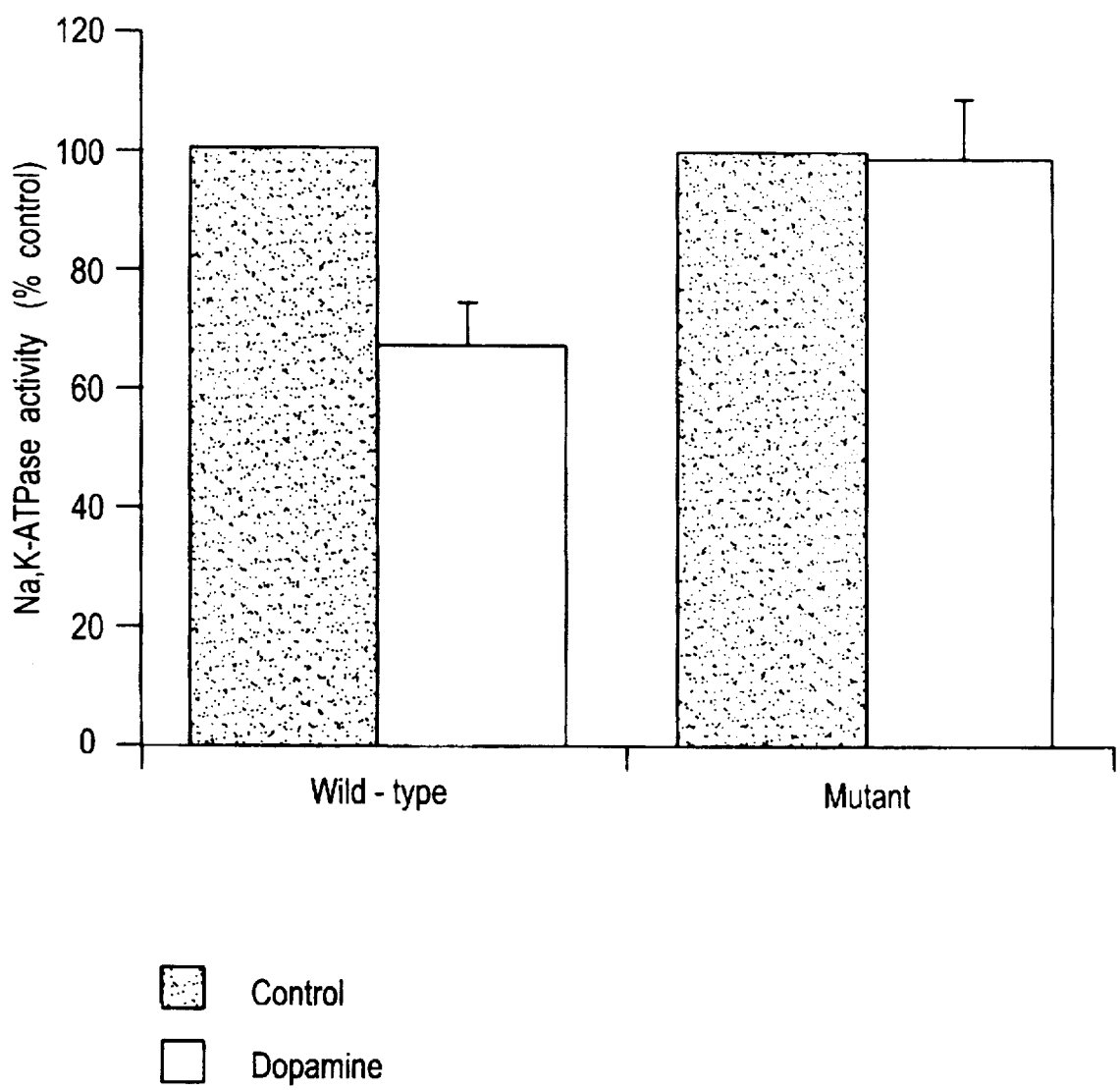
FIG. 3 shows the effect of dopamine on the activity of Na+, K+–ATPase as measured in striatal neurons of wild-type and DARPP-32 knockout mice. In wildtype mice dopamine inhibits the activity by approximately 30%. In mutant mice this effect is completely eliminated.

Embryonic stem cells are always derived from the strain 129 Sv and typically have a male genotype. This 129 Sv strain of mice has an agouti (beige) coat color. Pups born from embryos injected with embryonic stem cells will be chimeric, that is their somatic and germline tissue cells will contain cells from the host strain (typically C57B⅙) and the embryonic stem cell line (129Sv). Evidence of chimerism is obvious in the coat color of these animals as it will contain a mixture of black and agouti hair. Evidence that the embryonic stem cells have colonized the germline of the chimera is obtained by breeding the chimeric animals to C57B1/6 partners. Typically the chimeras are male and are thus bred to female C57B1/6 mice. Pups with an agouti coat born from these matings demonstrate that the germline of the chimera was derived, at least in part, from the injected embryonic stem cells. Given that the coat color of the animals is encoded by genes that are not necessarily linked to the gene that has been knocked out it must also be demonstrated that the subsequent offspring have the altered allele. Finally mice that type as heterozygotes are bred together in order to generate offspring with three genotypes; wildtype, heterozygote and mutant (see FIG. 1D "genotypes"). One confirms successful inactivation of the gene after immunoblot analysis of tissue that would normally contain the protein. Since mutants contain two copies of the inactivated gene, one predicts that mice that type as mutants will not make the protein. Immunoblots from striatum and cortex of all animals in a given mouse litter are shown in FIG. 1D. Note that mutants do not produce the DARPP-32 protein.

P. Preparation of genomic DNA from mice

1. Cut a 1 cm section from the end of a mouse tail and place in lysis buffer (100 mM Tris pH 8.8; 200 mM NaCl; I mM CaCl2 ; 0.2% SDS, just before use add proteinase K powder to a final concentration of 100 mg/ml)

2. Place tails in a 55° C. incubator—shake them slowly overnight.

3. The following morning the digested tails are vortexed mildly (about 3 sec) to resuspend the thick mixture.

4. Spin at 12,000 rpm 10 minutes, room temperature.

5. Pour (do not pipet) supernatant into new tubes.

6. Add 0.5 ml isopropanol.

7. Invert tubes about ten times or until you see a pellet.

8. Spin 4° C. 5–10 minutes.

9. Pour off supernatant, add 1 ml 70% ethanol to wash pellet. Spin briefly or longer if pellet becomes loose. Suck off supernatant completely. Let air dry (usually about 30 min.) until completely dry. Do not put into an oven to dry. This bakes the DNA and makes it hard to resuspend.

10. When dry add 150 ml TE. Put at 50–60° C. for several hours or overnight.

At this point, the DNA can be cut with most enzymes. However, for the Xba digestion required to assay the mutated allele in the DARPP-32 knockout, it is necessary to reprecipitate the DNA as follows:

11. Add NaCl to a final concentration of 0.2M. Add 2 volumes of 100% ethanol. Invert until a pellet is seen.

Spin at 12000 rpm for 10 min. Wash with 70 50% ethanol. Air dry as above.

Resuspend in 150 mL TE. Cut with restriction enzyme Xba using standard procedures (2).

EXAMPLE 2

Fundamental Neuronal Processes Affected by Knockout of the DARPP-32 Gene

A. Neuronal Physiology

1. Electrophysiology

Striatal neurons from the DARPP-32 knockout mouse show defects in the dopamine regulation of calcium channel function (FIG. 2). References for the assay procedures for these experiments can be found in (5). In striatal neurons, dopamine or a D1 agonist such APB, acts to inhibit calcium channel current. In the DARPP-32 knockout the inhibition of the current occurs normally but the reversal of that inhibition occurs much more slowly. Dopamine also acts to inhibit the activity of the sodium-potassium ATPase. In DARPP-32 mutants this inhibition is completely gone. Protocols for these experiments can be found in (6) In addition mutant mice show defects in mechanisms related to striatal neuron excitability such as the effect of dopamine on firing threshold (protocols are in (7).

2. GABA and dopamine release

Figure 4A:
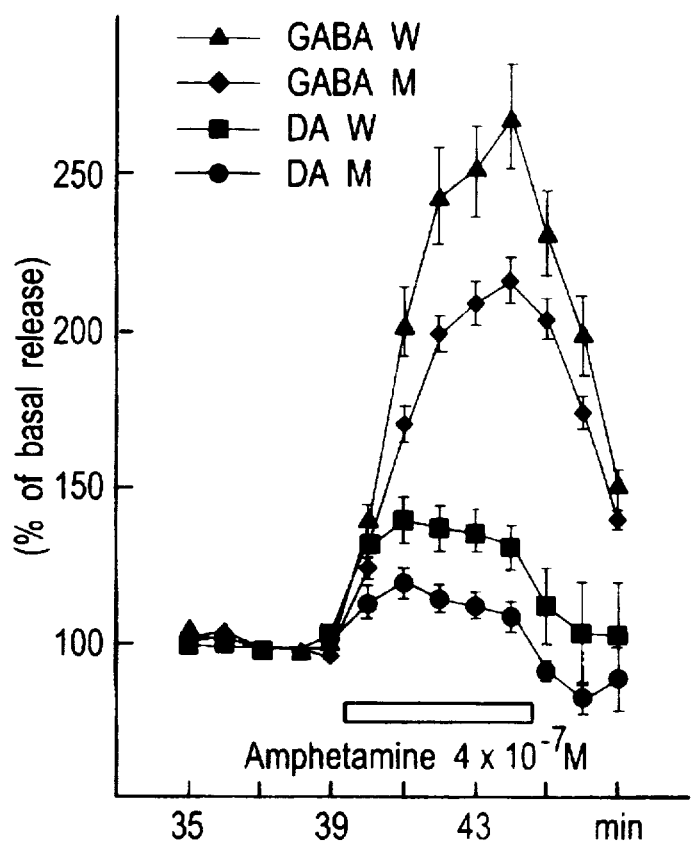
Figure 4B:
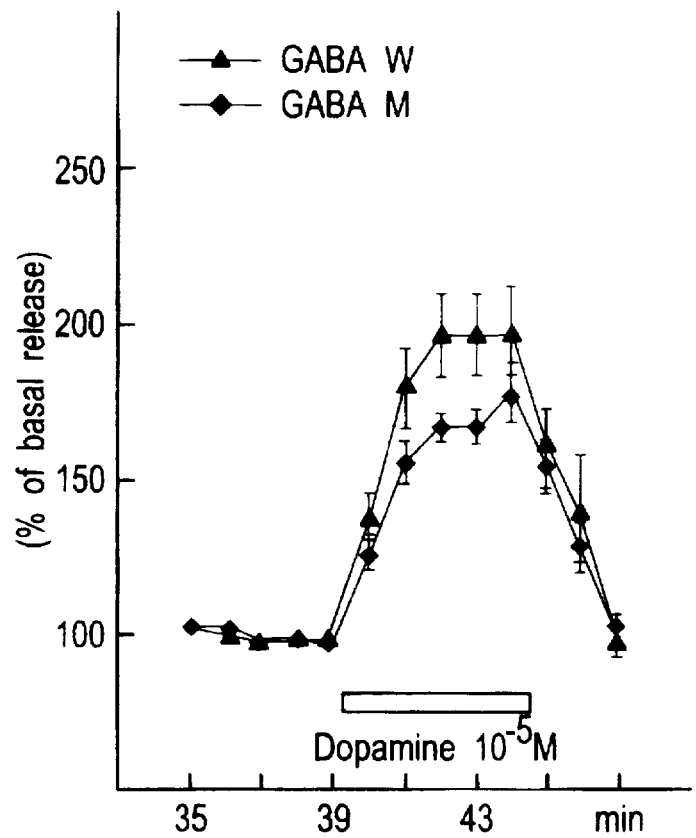

Deficiencies in the release of dopamine and GABA have also been observed (FIG. 4) (details of these protocols can be found in (8). In response to amphetamine in striatal micropunches, DARPP-32 mutants release approximately 25–30% less GABA and dopamine than wildtype mice. In addition, the release of GABA is also reduced in the DARPP-32 mutants in response to dopamine.

3. Neuropeptides

Figure 5A:
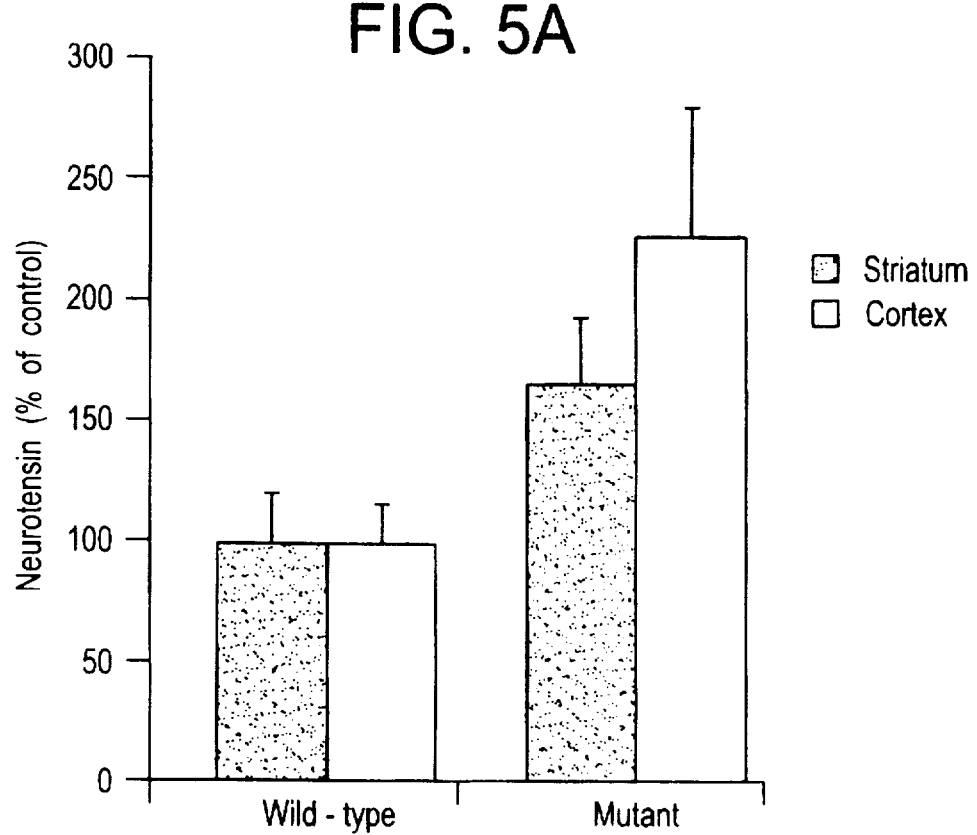
FIG. 5 is a graph that illustrates the quantitation of higher levels of neurotensin in striatum and cortex of mutant mice as compared to wildtypes.
FIG. 5B shows the quantitation of higher levels of substance P in the striatum and cortex of mutant mice as compared to wildtype mice.
Figure 5B:
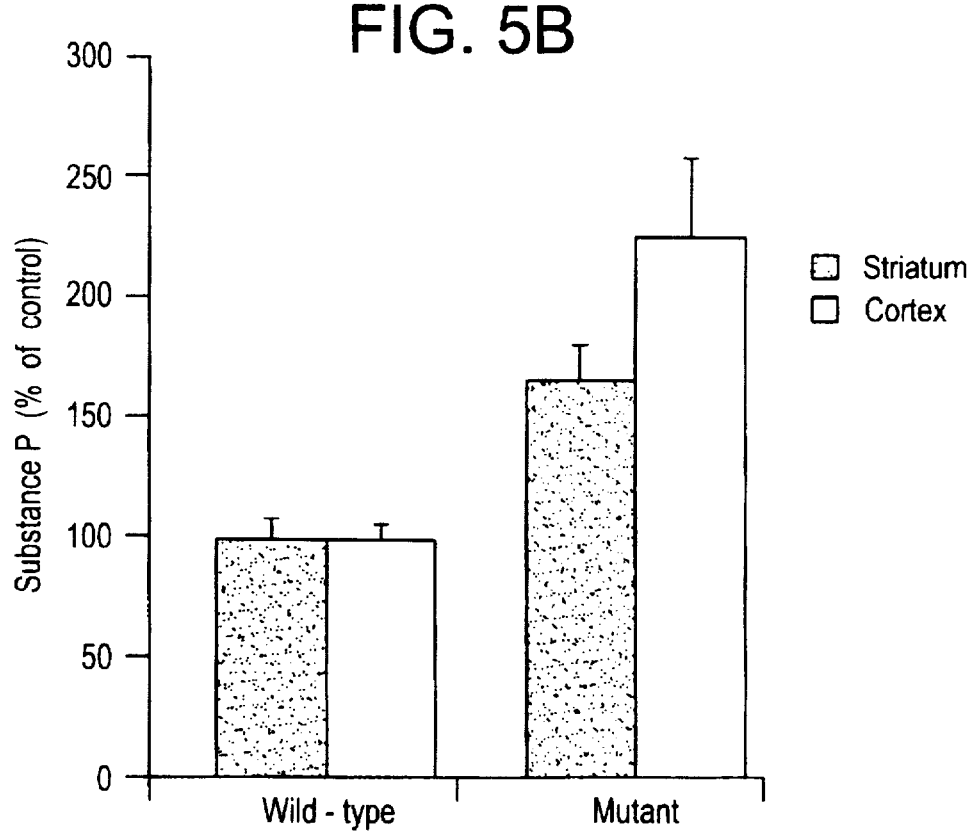

Increased levels (FIG. 5) of two neuropeptides, neurotensin and substance P, are seen in the cortex and striatum of mutant DARPP-32 mice as compared to wildtypes. These two substances can function as neurotransmitters (protocols for these experiments can be found in (9).

Taken together these results illustrate that DARPP-32 has several regulatory functions in striatal neurons and other neurons affected by dopamine.

B. Drugs of Abuse

Several of the effects of drugs of abuse have been examined in mice lacking DARPP-32

1. Locomotion

Figure 6:
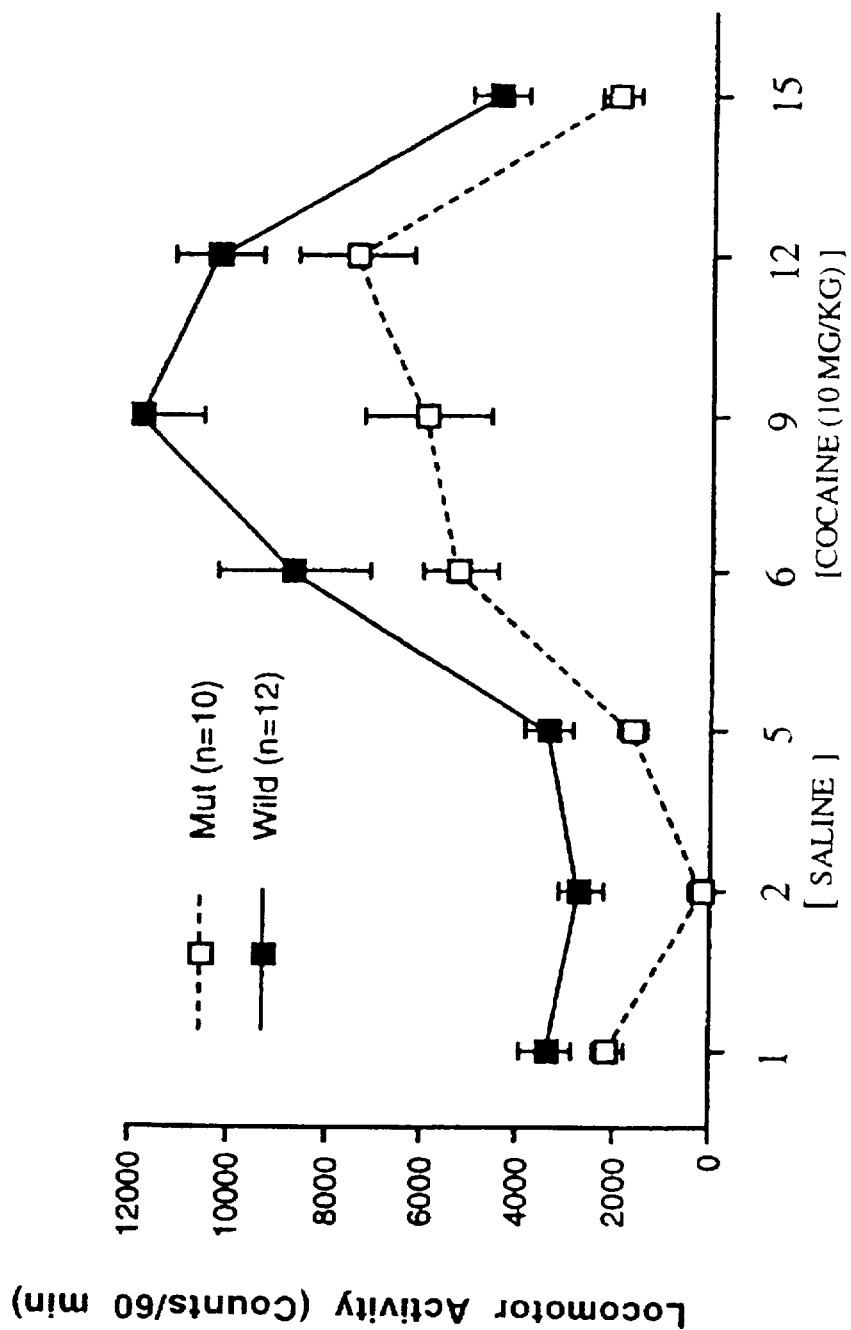
FIG. 6 is a graph of Horizontal Ambulatory Activity Counts in response to 10 mg/kg of cocaine in wildtype and mutant mice. Note that saline is given on Days 2–5 while cocaine is given on Day 6–12.

Administration of drugs of abuse to mice results in increases in locomotor activity. This increase serves as an assay for the effect of these drugs in animals. Mice lacking DARPP-32 do not show the same increases in locomotion as were seen in wild type animals (FIG. 6). Details for these experiments can be found in (10) These results imply that DARPP-32 functions in the pathway by which drugs of abuse act in an animal.

2. Induction of Fos and Chronic Fra

Figure 7:
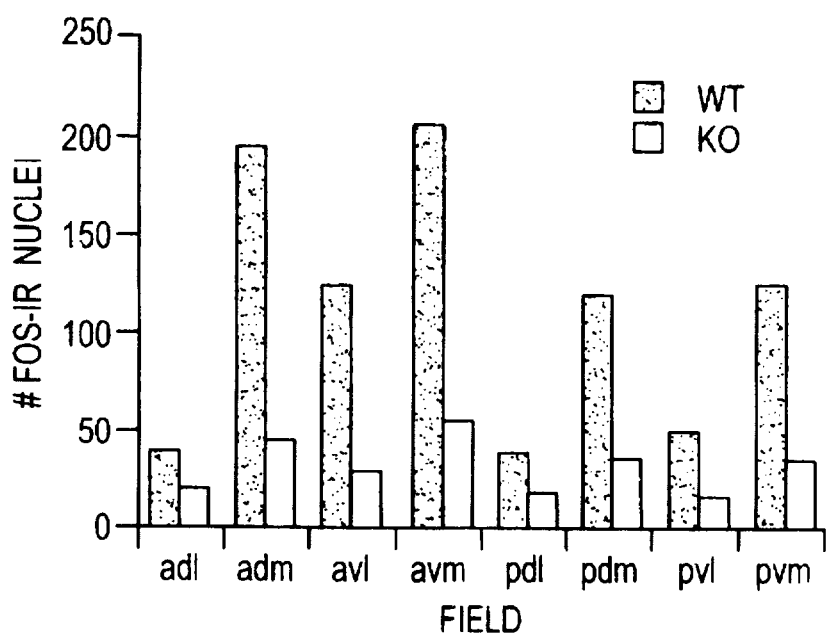
FIG. 7 is a plot of the induction of fos immunoreactive nuclei seen 24 hrs after the administration of one dose of 10 mg/kg of amphetamine to wildtype and mutant mice. In each animal a coronal section of the striatum is made which is subsequently divided into quadrants. a=anterior; p=posterior; d=dorsal; v=ventral; l=lateral; m=medial.
Figure 8:
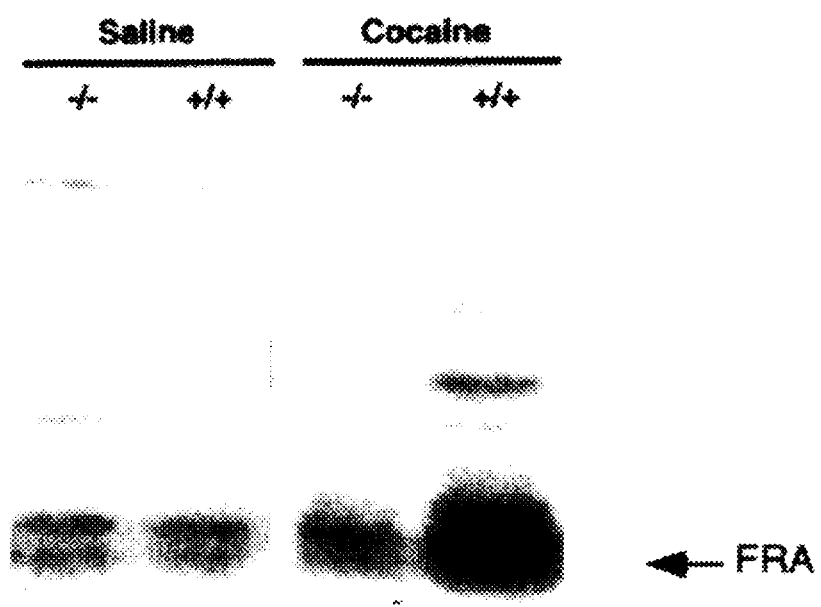
FIG. 8 is an immunoblot of striatal proteins illustrating the induction of the chronic FRA protein in wildtype (+/+) but not mutant (−/−) mice after the administration of cocaine for seven consecutive days.

A single dose of amphetamine to mice results in the induction in the striatum of a protein called fos. Mice lacking DARPP-32 show a significantly attenuated induction of this protein (FIG. 7). This is an assay that measures the acute effects of this psychostimulant. Chronic administration of cocaine results in the induction of a protein called chronic Fra. The induction of this protein was also severely attenuated in the DARPP-32 mutant mouse (FIG. 8). These results demonstrate at the intracellular level that DARPP-32 functions in an intracellular signaling pathway that is activated by both the acute and chronic effects of psychostimulants. Details for how these experiments were carried out can be found in (11)

3. Self-administration

Mice can be trained to press a lever in order to receive an injection of cocaine directly into the bloodstream. This assay has the closest similarity to drug taking in humans. Preliminary studies show that mice lacking DARPP-32 show a diminished desire to work for the administration of cocaine implying that DARPP-32 is a biological target in the addiction process.

C. Renal Physiology

Mice lacking DARPP-32 show decreased sodium excretion (Table 1), increased fluid retention and altered ANF-mediated regulation of the sodium-potassium ATPase in kidney tubules similar to what is seer in striatal neurons. Preliminary studies suggest that defects in renal physiology lead to high blood pressure [hypertension] in mice lacking DARPP-32. Protocols for these studies can be found in (15) and (16). These defects are elicited by sodium loading these DARPP-32 deficient mice.

Table 1, below show the excretion of urinary Na+in wildtype and mutant in response to a trial natriuretic peptide (ANF). Urinary excretion (in response to ANF) increases in wildtype mice by approximately four-fold. In mutant mice this increase does not occur.

TABLE 1

| URINARY Na EXCRETION (µMOL/MIN) | | |
|---|---|---|
| Infusion | Wild-Type | DARPP-32 Knock-Out |
| Saline | 0.10 | 0.16 |
| ANF | 0.42 | 0.09 |

D. Animal Behavior

Figure 9:
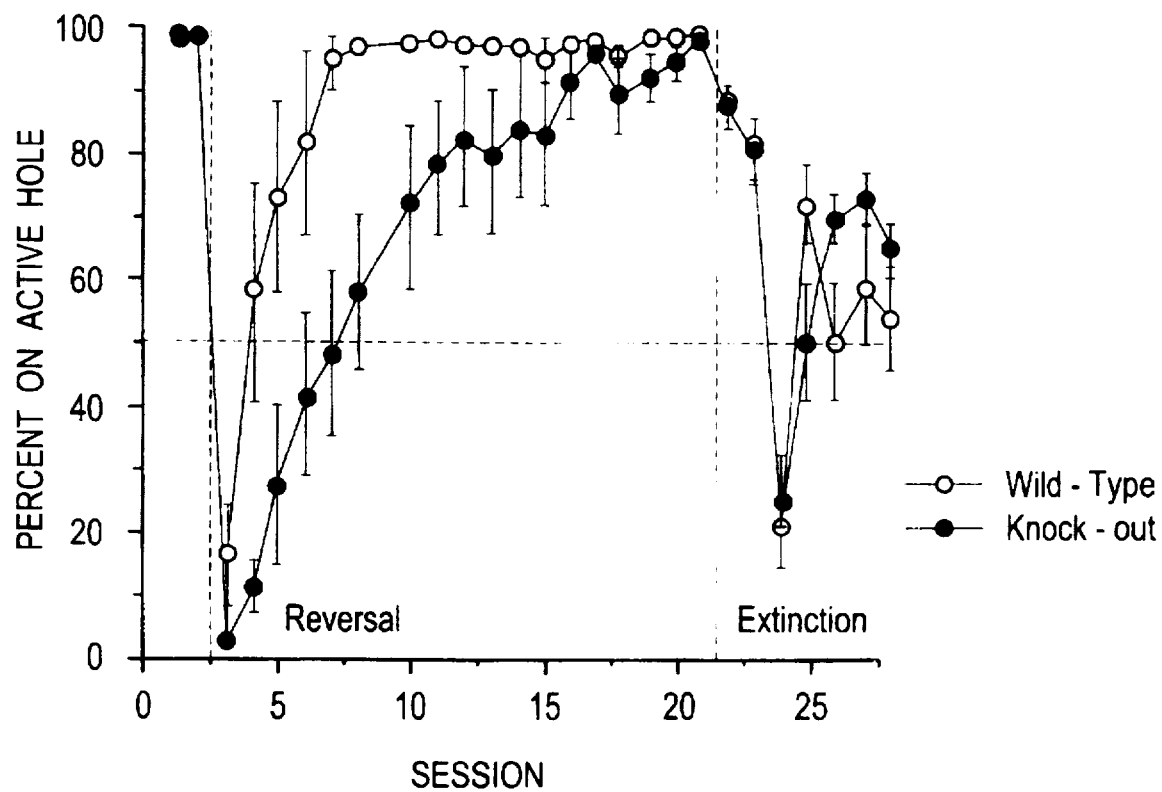
FIG. 9 is a plot of food reinforced operant responding in wildtype vs mutant mice. Discrimination index is calculated as active responses/total responses. Plot demonstrates that before reversal of the active and inactive holes there is no difference between wildtype and mutant mice. After reversal, the mutant mice are significantly delayed in their ability to learn the new response contingency. Wildtype mice demonstrate a 100% discrimination index by six days after reversal while it took mutant mice 18 days to maintain consistent responding at that level.

In a study designed as a control for the self-administration studies described in B.3, DARPP-32 mutant mice showed defects in a task referred to as "reversal" (FIG. 9). Numerous studies in humans have shown that schizophrenic patients show specific defects in this same task (12). Details for the protocols followed in these experiments can be found in (13,14).

Another animal behavior, called prepulse inhlibilioni (PPI), also has similarities to behaviors seen in schizophrenic patients. Prepulse inhibition is the normal reduction in startle reflex that occurs when a startling stimulus, such as a blast of sound, is preceded by a weak prepulse. This startle reflex is reduced in patients with schizophrenia and in rats after administration of dopamine agonists. In order to assay the startle response in this assay, wildtype and DARPP-32 mutant mice are placed in startle chambers (SR-LAB, San Diego Instruments, San Diego, Calif.) housed in a sound attenuated room. Animals are placed in a plexiglass frame and acoustic noise bursts are presented via a speaker mounted above the animal. A piezoelectric accelerometer mounted below the animal transduces the motion of the animal within the frame. Wildtype and DARPP-32 mutant mice are assayed in this apparatus. DARPP-32 mutants display less prepulse inhibition in response to dopamine agonists than wildtype animals consistent with the role of DARPP-32 in dopamine signaling. Details for these experiments can be found in Wan et al., *Psychopharmacology* 120:433–441 (1995).

The following is a list of documents related to the above disclosure and particularly to the experimental procedures and discussions. These documents, and all others cited above, should be considered as incorporated by reference in their entirety.

1. Walaas, S. I., D. W., A., and P., G. (1983) Nature 301, 69–71.

2. Sambrook, J., Fritsch, E. F., and Maniatis, T. (1989) Molecular Cloning: A Laboratory Manual. (Nolan, C., Ed.), Cold Spring Harbour Laboratory Press.

3. te Riele, H., Maandag, E. R., and Berns, A. (1992) Proc. Natl. Acad. Sci. USA 89, 5128–5133.

4. Joyner, A. L. (1993) Gene Targeting: A Practical Approach. The Practical Approach Series (Rickwood, D., and Hames, B. D., Eds.), IRL Press, Oxford.

5. Surmeier, D. J., Bargas, J., H. C. Jr., H. Nairn, A. C., and Greengard, P. (1995) Neuron 14, 385–397.

6. Bertorello, A. M., Hopfield, J. F., Aperia, A., and Greengard, P. (1990) Nature 347(6291), 386–8.

7. Calabresi, P., Mercuri, N., Stanzione, P., Stefani, A., and Bernardi, G. (1987) Neuroscience 20(3), 757–71.

8. Girault, J. A., Spampinato, U., Glowinski, J., and Besson, M. J. (1986) Neuroscience 19(4), 1109–1117.

9. Hanson, G. R., Merchant, K. M., Letter, A. A., Bush, L., and Gibb, J. W. (1987) Eur. J. Pharmi. 144, 245–246.

10. Kosten, T. A., Miserendino, M. J. D., Chi, S., and Nestler, E. J. (1994) J. Pharmacol. Exp. Ther. 269, 137–144.

11. Hope, B., Kosofsky, B., Hyman, S. E., and Nestler, E. J. (1992) Proceedings of the National Academy of Sciences of the United States of America 89(13), 5764–8.

12. Ridley, R. M. (1994) Prog. Neuro. 44, 221–231.

13. Caine, S. B., and Koob, G. F. (1994) Journal of the Experimental Analysis of Behavior 61(2), 213–21.

14. Caine, S. B., and Koob, G. F. (1995) Behav. Pharm. (in press).

15. Aperia, A., Ibarra, F., Svensson, L. B., Klee, C., and Greengard, P. (1992) Proc. Natl. Acad. Sci. USA 89, 7394–7397.

16. Korner, A., Eklof, A. C., Celsi, G., and Aperia, A. (1994) Diabetes 43, 629–633.

What is claimed is:

1. A transgenic knockout mouse comprising a homozygous disruption in its endogenous DARPP-32 gene, wherein said disruption prevents the expression of a functional DARPP-32 protein, and further wherein the phenotype of said knockout mouse relative to a mouse having a wild type DARPP-32 gene comprises:

i) a diminished response to dopamine wherein said diminished response includes a failure of dopamine to inhibit the activity of brain sodium-potassium ATPase;

ii) a diminished release of dopamine in response to amphetamine administration; and iii) an increased level of substance P in the striatum and cortex.

2. The knockout mouse of claim 1, wherein the disruption comprises an insertion into the first exon of the DARPP-32 gene.

3. The knockout mouse of claim 2, wherein the insertion replaces DNA at the start of the coding region of the DARPP-32 protein.

4. The knockout mouse of claim 1, wherein the phenotype of said mouse relative to a mouse having a wild type DARPP-32 gene further comprises a phenotype selected from the group consisting of:

i) a diminished release of GABA in response to amphetamine administration;

ii) an attenuated increase in fos protein in response to amphetamine administration;

iii) an attenuated increase in the protein Chronic fos related antigen (FRA) in response to cocaine administration;

iv) a failure of Atrial Natriuretic Factor (ANF) to inhibit the activity of renal sodium-potassium ATPase;

v) a loss of Atrial Natriuretic Factor (ANF) mediated increases in sodium excretion.

5. A method for producing the knockout mouse of claim 1 comprising:

(a) obtaining genomic DNA encoding a portion of DARPP-32;

(b) constructing a vector containing said genomic DNA and a marker gene, wherein said marker gene is inserted into an exon of said genomic DNA;

(c) introducing said vector into mouse embryonic stem cells by electroporation;

(d) selecting a cell that has a disrupted DARPP-32 gene due to the integration of said vector into its genome by homologous recombination into the endogenous DARPP-32 gene;

(e) injecting said cell into a mouse blastocyst, thereby forming a chimeric blastocyst;

(f) implanting said resultant chimeric blastocyst into a pseudopregnant mouse wherein said pseudopregnant mouse gives birth to a chimeric mouse containing a mutant DARPP-32 gene in its germ line;

(g) breeding said chimeric mouse to generate a heterozygous mouse comprising a disrupted DARPP-32 gene thereby generating a mouse heterozygous for said disrupted DARPP-32 gene; and (h) mating together a male and a female mouse each heterozygous for said disrupted DARPP-32 gene and selecting progeny that are homozygous for said disrupted DARPP-32 gene.

6. A method for selecting a potential therapeutic agent for use in the treatment of schizophrenia, comprising:

(a) administering a potential therapeutic agent to the knockout mouse of claim 1;

(b) measuring the response of said knockout mouse to said potential therapeutic agent;

(c) comparing the response of said knockout mouse with that of a mouse having a wild type DARPP-32 gene; and (d) selecting a potential therapeutic agent based on the difference in responses observed between said knockout mouse and said mouse having a wild type DARPP-32 gene.

7. A method for selecting a potential therapeutic agent for use in the treatment of schizophrenia, comprising:

(a) administering a potential therapeutic agent to the knockout mouse of claim 1, (b) measuring the response of said knockout mouse to administration of a neurotransmitter that interacts with the dopamine signaling pathway;

(c) comparing the response of said knockout mouse with that of a mouse having a wild type DARPP-32 gene; and (d) selecting a potential therapeutic agent based on the difference in responses observed between said knockout mouse and said mouse having a wild type DARPP-32 gene.

8. A method for selecting a potential therapeutic agent for use in the treatment of Parkinson's Disease, comprising:

(a) administering a potential therapeutic agent to the knockout mouse of claim 1;

(b) measuring the response of said knockout mouse to dopamine administration;

(c) comparing the response to dopamine administration of said knockout mouse with that of a mouse having a wild type DARPP-32 gene; and (d) selecting a potential therapeutic agent based on the difference in responses observed between said knockout mouse and said mouse having a wild type DARPP-32 gene.

9. A method for selecting a potential therapeutic agent for use in the treatment of Parkinson's Disease, comprising:

(a) administering a potential therapeutic agent to the knockout mouse of claim 1;

(b) measuring the response of said knockout mouse to administration of a neurotransmitter that interacts with the dopamine signaling pathway;

(c) comparing the response of said knockout mouse with that of a mouse having a wild type DARPP-32 gene; and (d) selecting a potential therapeutic agent based on the difference in responses observed between said knockout mouse and said mouse having a wild type DARPP-32 gene.

10. A method for selecting a potential therapeutic agent for use in the treatment of addictive behaviors towards addictive drugs, comprising:

(a) administering a potential therapeutic agent to the knockout mouse of claim 1;

(b) measuring the response of said knockout mouse;

(c) comparing the response of said knockout mouse with that of a mouse having a wild type DARPP-32 gene; and (d) selecting a potential therapeutic agent based on the difference in responses observed between said knockout mouse and mouse having a wild type DARPP-32 gene.

11. A method for selecting a potential therapeutic agent for use in the treatment of addictive behaviors towards addictive drugs, comprising:

(a) administering a potential therapeutic agent to the knockout mouse of claim 1;

(b) measuring the response of said knockout mouse to administration of a neurotransmitter that interacts with the dopamine signaling pathway;

(c) comparing the response of said knockout mouse with that of a mouse having a wild type DARPP-32 gene; and (d) selecting a potential therapeutic agent based on the difference in responses observed between said knockout mouse and said mouse having a wild type DARPP-32 gene.

12. A method for selecting a potential therapeutic agent for use in the treatment of hypertension, comprising:

(a) administering a potential therapeutic agent to the knockout mouse of claim 1;

(b) measuring the response of said knockout mouse to administration of a factor selected from the group consisting of a natriuretic factor and an anti-natriuretic factor;

(c) comparing the response of said knockout mouse with that of a mouse having a wild type DARPP-32 gene; and (d) selecting a potential therapeutic agent based on the difference in responses observed between said knockout mouse and said mouse having a wild type DARPP-32 gene.

13. The method of claim 12 wherein said anti-natriuretic factor is Atrial Natriuretic Factor.

14. A method for selecting a potential therapeutic agent for use in the treatment of hypertension, comprising:

(a) administering a potential therapeutic agent to a knockout mouse of claim 1 wherein said disruption of DARPP-32 results in a renal pathology that leads to high blood pressure;

(b) measuring the response of said knockout mouse to administration; and (c) selecting a potential therapeutic agent based on the ability of said potential therapeutic agent to lower blood pressure in said knockout mouse.

15. The method of claim 14 wherein the high blood pressure is elicited by sodium loading of said knockout mouse.

* * * * *